United States Patent
Natori

(10) Patent No.: US 7,130,043 B2
(45) Date of Patent: Oct. 31, 2006

(54) LASER SCANNING MICROSCOPE AND INDICATOR DISCRIMINATING METHOD

(75) Inventor: Yasuaki Natori, Ina (JP)

(73) Assignee: Olympus Corporation, Tokyo (JP)

(\*) Notice: Subject to any disclaimer, the term of this patent is extended or adjusted under 35 U.S.C. 154(b) by 361 days.

(21) Appl. No.: 10/833,717

(22) Filed: Apr. 27, 2004

(65) Prior Publication Data

US 2004/0218174 A1 Nov. 4, 2004

(30) Foreign Application Priority Data

Apr. 30, 2003 (JP) ............................ 2003-125650

(51) Int. Cl.
*G01N 21/64* (2006.01)

(52) U.S. Cl. .................................. 356/318; 250/458.1
(58) Field of Classification Search ............ 250/458.1, 250/461.1; 356/318
See application file for complete search history.

(56) References Cited

U.S. PATENT DOCUMENTS 6,958,811 B1\* 10/2005 Wolleschensky et al. ... 356/326

FOREIGN PATENT DOCUMENTS

| JP | 2000-56244 A | 2/2000 |
| JP | 2001-124997 A | 5/2001 |
| JP | 2002-55284 A | 2/2002 |

\* cited by examiner

*Primary Examiner*—F. L. Evans
(74) *Attorney, Agent, or Firm*—Frishauf, Holtz, Goodman & Chick, P.C.

(57) ABSTRACT

A laser beam is scanned on a sample while a wavelength of the laser beam is varied. Quantity of fluorescence from the sample is detected. Absorption wavelength spectral characteristic data of fluorescence indicators whose kinds are known and which dye the sample is acquired. The absorption wavelength spectral characteristic data of a site to be discriminated is compared with the absorption wavelength spectral characteristic data of each of the fluorescence indicators of known kinds. The kind of fluorescence indicator dyeing the site to be discriminated is discriminated from a result of the comparison.

20 Claims, 5 Drawing Sheets

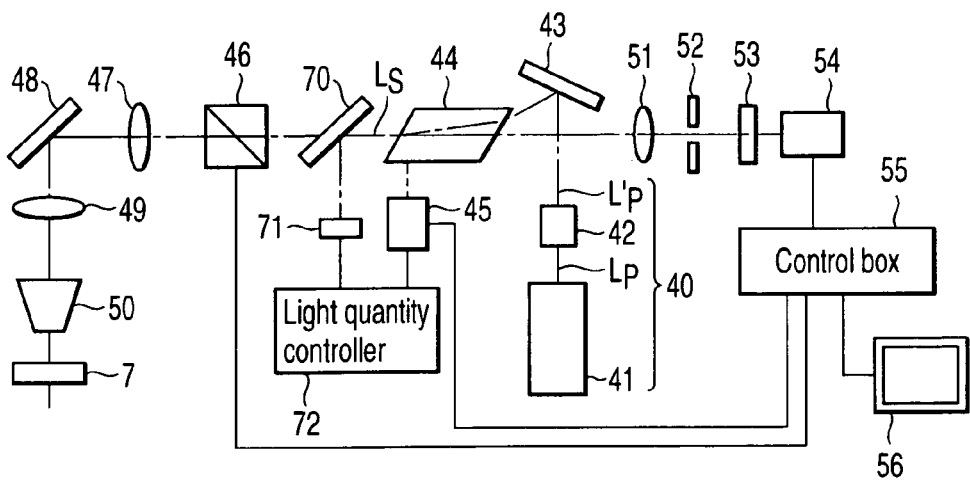
F I G. 8

LASER SCANNING MICROSCOPE AND INDICATOR DISCRIMINATING METHOD

CROSS-REFERENCE TO RELATED APPLICATIONS

This application is based upon and claims the benefit of priority from prior Japanese Patent Application No. 2003-125650, filed Apr. 30, 2003, the entire contents of which are incorporated herein by reference.

BACKGROUND OF THE INVENTION

1. Field of the Invention

This invention relates to a laser scanning microscope capable of scanning a laser beam onto a sample dyed with a fluorescence indicator and detecting fluorescence from the sample, and, an indicator discriminating method for discriminating the kind of fluorescence indicator dyeing the sample by using absorption wavelength spectral characteristics of the detected fluorescence.

2. Description of the Related Art

A laser scanning microscope is disclosed in, for example, Jpn. Pat. Appln. KOKAI Publication No. 2000-56244 and Jpn. Pat. Appln. KOKAI Publication No. 2002-55284. FIG. 9 shows a structure of the laser scanning microscope of Jpn. Pat. Appln. KOKAI Publication No. 2000-56244. The laser scanning microscope comprises a microscope 1 and a scanning device 2. The microscope 1 comprises a light source 3, an illumination lens system 4, a beam splitter 5, an objective 6, a stage 7 over which a sample S is placed, a condenser 8, a light source 9, a transmitted light detector 10, an image-forming lens 11, a beam splitter/mirror 12 and an eyepiece 13.

The scanning device 2 comprises a laser unit 14, a shutter 15, a collimation lens system 16, beam splitters 17 and 18, a scanning means 19, a confocal pinhole 20, a grating 21, image-forming mirrors 22 and 23, a one-dimensional change mirror array (DMD) 24, a converging lens system 25, and a detector 26.

The confocal pinhole 20 is provided at a conjugate position via the objective 6. A monochromator is composed of the grating 21 and the image-forming mirrors 22 and 23. The confocal pinhole 20 serves as an incidence opening of the monochromator. The change mirror array 24 is provided on a focal plane of the grating 21.

The laser unit 14 outputs a laser beam. The laser beam is passed through the shutter 15, the collimation lens system 16 and the beam splitters 17 and 18 and made incident on the scanning means 19. The laser beam is scanned, for example, in a direction X-Y by the scanning means 19. The laser beam scanned in the direction X-Y is reflected by the beam splitter/mirror 12, passed through the image-forming lens 11, the beam splitter 5 and the objective 6, and scanned over the sample S placed on the stage 7.

Fluorescence emitted from the sample S is made incident on the beam splitter/mirror 12 after passing through the objective 6, the beam splitter 5 and the image-forming lens 11. The fluorescence is reflected by the beam splitter/mirror 12, passed through the scanning means 19 and the beam splitter 18, and made to come into a focus on the confocal pinhole 20. The confocal pinhole 20 serves as an incidence opening of the monochromator composed of the grating 21, and the image-forming mirrors 22 and 23. The light beam from the sample S is split into spectral components by the dispersion effect of the monochromator.

The one-dimensional change mirror array 24 which can be arbitrarily programmed is, at least, provided on the focal plane of the grating 21. Thus, an image of the spectral light beam, from the sample S is optically formed on the change mirror array 24, converged by the converging lens system 25 and detected by the detector 26. By programming the change mirror array 24 in the above-described manner, the fluorescence wavelength spectral characteristics of the sample S can be obtained.

FIG. 10 shows a structure of the scanning microscope disclosed in Jpn. Pat. Appln. KOKAI Publication No. 2002-55284. Laser beam $L_1$ output from a laser light source 30 is spectrally spread by an optical device 31 to be wideband spectral illumination light $L_2$. The spectral illumination light $L_2$ is introduced into an AOTF (acousto-optic tunable filter) 32 and wavelength-selected. The wavelength-selected spectral light $L_3$ is passed through a beam splitter 34, a scanning mirror 35 and an objective 36 and applied onto a sample S. The light beam reflected or emitted from the sample S returns in a direction reverse to the path for irradiation onto the sample S. Thus the light beam is passed through the beam splitter 34 and made incident on a detector 37.

As the optical device 31 outputs wideband spectral illumination light $L_2$, the light quantity needs to be constant by selecting the wavelength. For this reason, an acousto-optically or electro-optically tunable filter (AOTF) may be combined with an acousto-optic or electro-optic deflector (AOD) and an acousto-optic or electro-optic beam splitter (AOBS) disclosed in Jpn. Pat. Appln. KOKAI Publication No. 2001-124997. The acousto-optic or electro-optic deflector (AOD) and the acousto-optic or electro-optic beam splitter (AOBS) can be employed to select the wavelength and stop down the detected light.

In observation of the sample S dyed with the fluorescence indicator, the kind of the fluorescence indicator needs to be discriminated. In Jpn. Pat. Appln. KOKAI Publication No. 2000-56244, the fluorescence from the sample S is split into spectral contents by the dispersion effect of the monochromator composed of the grating 21 and the image-forming mirrors 22 and 23 and the light quantity in each of the wavelengths of the spectrum is detected by the detector 26. The quantity of the fluorescence from the sample S is small. The quantity of light in each of the wavelengths is further reduced by splitting the fluorescence from the sample S into the spectral contents. The SN ratio of detecting the fluorescence by the detector 26 is smaller. For this reason, the detected quantity of the fluorescence is very small and a fluorescent image becomes dark. If the quantity of the fluorescence is too small, the quantity of light in each of the wavelengths cannot be detected by the detector 26. As a result, the kind of fluorescence indicator dyeing the sample S cannot be discriminated with the fluorescence wavelength spectral characteristics.

Jpn. Pat. Appln. KOKAI Publication No. 2002-55284 does not suggest anything about discrimination of the kind of fluorescence indicator dyeing the sample S.

BRIEF SUMMARY OF THE INVENTION

According to an aspect of the present invention, there is provided a laser scanning microscope comprising a laser output, a scanning unit, a light detector, a data acquiring unit, and a discriminating unit. The laser output unit is capable of outputting a laser beam and arbitrarily selecting a wavelength of the laser beam. The scanning unit scans the laser beam output from the laser output unit over a sample having a site dyed with at least one kind of fluorescence indicator. The light detector detects quantity of fluorescence emitted from the sample over which the laser beam is scanned. The data acquiring unit acquires data of the fluorescence quantity detected by the light detector while varying the wavelength of the laser beam output from the laser output unit to obtain absorption wavelength spectral characteristic data of the sample from the fluorescence quantity data. The discriminating unit discriminates the kind of fluorescence indicator dyeing the site in accordance with scanning position information obtained by scanning the laser beam on the sample by the scanning unit and the absorption wavelength spectral characteristic data.

According to another aspect of the present invention, there is provided a method of discriminating a fluorescence indicator. The method comprises scanning a laser beam over a sample dyed with a fluorescence indicator while varying a wavelength of the laser beam, measuring quantity of fluorescence emitted from at least a site of the sample to be measured, acquiring an absorption wavelength spectral characteristic of the measured site from the quantity of the fluorescence, acquiring absorption wavelength spectral characteristic data of a plurality of known fluorescence indicators whose kinds are known and which dye the sample, and comparing the absorption wavelength spectral characteristic data of the measured site with the absorption wavelength spectral characteristic data of the fluorescence indicators whose kinds are known, and discriminating the kind of fluorescence indicator dyeing the measured site from a result of the comparison.

BRIEF DESCRIPTION OF THE SEVERAL VIEWS OF THE DRAWING

FIG. 8 is a diagram showing a laser scanning microscope according to a second embodiment of the present invention;

DETAILED DESCRIPTION OF THE INVENTION

A first embodiment of the present invention will be explained below with reference to the accompanying drawings.

Figure 1:
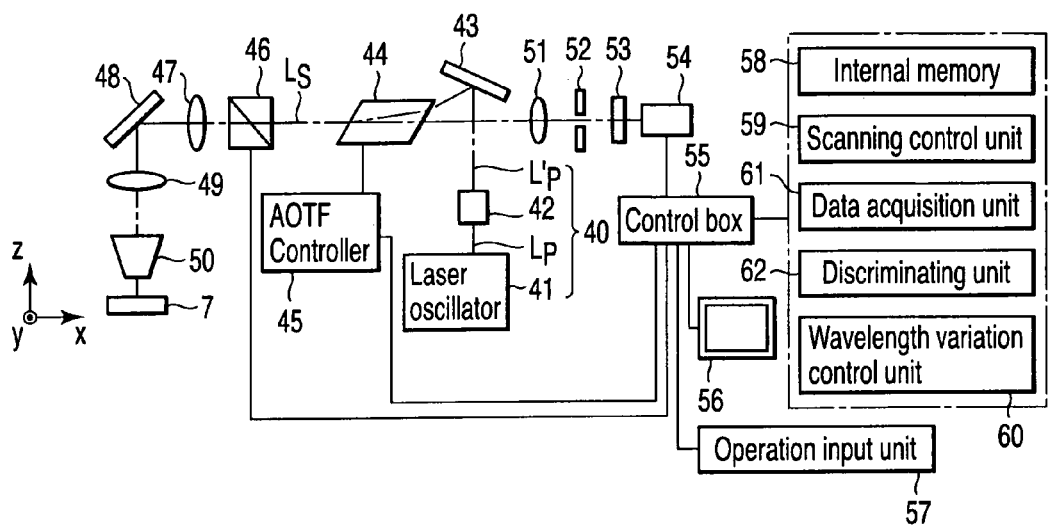
FIG. 1 is a diagram showing a laser scanning microscope according to a first embodiment of the present invention.

FIG. 1 shows a structure of a laser scanning microscope. A laser light source unit 40 comprises a laser oscillator 41 and an optical device 42. The laser oscillator 41 oscillates pulse laser beam Lp of femto-seconds. The optical device 42 is provided in a light path of the pulse laser beam Lp oscillated by the laser oscillator 41. The optical device 42 is formed of a photonic bandgap material. The optical device 42 converts the pulse laser beam Lp into wideband spread spectrum light beam Lp'.

A mirror 43 is provided in an optical path of the spread spectrum light beam Lp' output from the optical device 42. A filter 44 is provided in a reflected optical path of the mirror 43. The filter 44 comprises an AOTF (acousto-optic tunable filter). The filter 44 will be explained below as AOTF 44.

An AOTF controller 45 is connected to the AOTF 44. The AOTF controller 45 supplies an RF signal (radio frequency signal) in accordance with the selected wavelength. The AOTF 44 receives the RF signal from the AOTF controller 45, selects an arbitrary wavelength of the spread spectrum light beam Lp', and outputs spectrum Ls of the selected wavelength. To make the quantity of light constant, the AOTF 44 may be a combination of an acousto-optic or electro-optic deflector (AOD) or a combination of an acousto-optic device and an electro-optic beam splitter (AOBS).

An XY scanner 46, a pupil projection lens 47 and a mirror 48 are provided in an optical path of the spectrum Ls which is output from the AOTF 44. An image-forming lens 49 and an objective 50 are provided in a reflected optical path of the mirror 48.

A confocal lens 51, a confocal aperture 52, a laser cut filter 53 and a photoelectric conversion device 54 (example, photo multiplier tube=PMT) are provided in a transparent optical path of the AOTF 44 on a side opposite to the side where the XY scanner 46 is provided. The confocal aperture 52 is provided at an optically conjugate position with a surface of the sample S. The laser cut filter 53 allows only light of a specific wavelength band to pass therethrough. The photoelectric conversion device 54 outputs a light quantity detection signal in accordance with the quantity of the fluorescence emitted from the sample S.

A display unit 56 and an operation input unit 57 are connected to a control box 55. The display unit 56 is, for example, a CRT display, a liquid crystal display or the like. The operation input unit 57 is, for example, a keyboard, a mouse or the like. The control box 55 comprises an internal memory 58.

The control box 55 stores in the internal memory 58 a wavelength range and a wavelength resolution to acquire absorption wavelength spectral characteristics input from the operation input unit 57, cooperates of a region on a surface of the sample S to acquire the absorption wavelength spectral characteristics, and the like.

The control box 55 inputs the light quantity detection signal output from the photoelectric conversion device 54 and stores fluorescence quantity data acquired by a data acquiring unit 61 to be explained later.

The control box 55 further comprises a scanning control unit 59, a wavelength variation control unit 60, a data acquisition unit 61 and a discriminating unit 62. The scanning control unit 59 transmits a scanning control signal to the XY scanner 46 in accordance with a preset scanning range of the laser beam over the sample S. The scanning range of the laser beam is included in, for example, a certain region over the sample or a region corresponding to 1-pixel region on fluorescent image data. The fluorescent image data is used when the fluorescence quantity data is displayed on the display unit 56.

The wavelength variation control unit 60 transmits a wavelength control signal to sequentially vary the wavelength to the AOTF controller 45.

The data acquisition unit 61 inputs the light quantity detection signal which is output from the photoelectric conversion device 54 while synchronizing with variation of the wavelength of the spectrum Ls output from the AOTF 44, acquires and stores the fluorescence quantity data from the input light quantity detection signal, in the internal memory 58, and performs an operation of the data to acquire the absorption wavelength spectral characteristics data of the sample S. The data acquisition unit 61 stores the acquired absorption wavelength spectral characteristics data for each pixel in the internal memory 58.

The discriminating unit 62 discriminates the kind of fluorescence indicator dyeing the sample S on the basis of the scanning position information of the spectrum Ls over the sample S obtained by the XY scanner 46 and the absorption wavelength spectral characteristics data acquired by the data acquisition unit 61.

Next, operations of the laser scanning microscope having the above-explained structure will be described.

Figure 2:
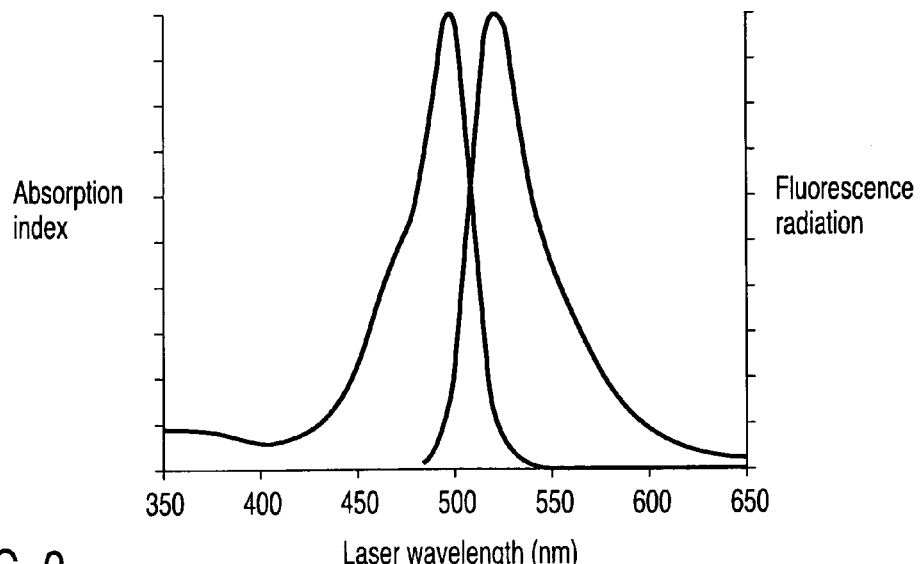
FIG. 2 is a graph showing absorption wavelength spectral characteristics of a fluorescence indicator dyeing a sample.
Figure 3:
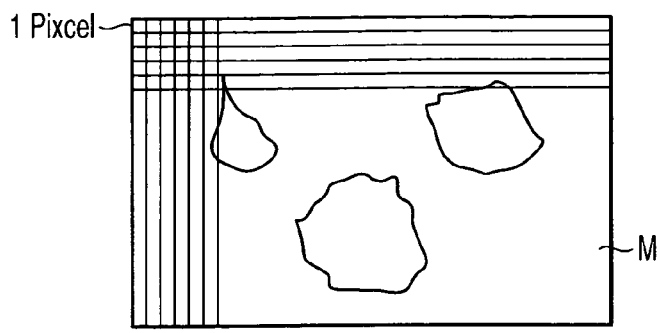
FIG. 3 is a pictorial illustration showing a region where the absorption wavelength spectral characteristics of each pixel are obtained.
Figure 4:
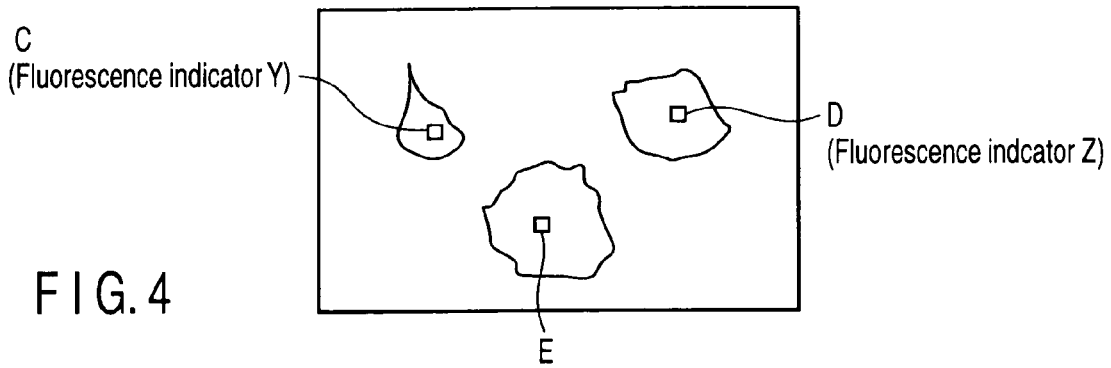
FIG. 4 is an illustration showing fluorescent image data of a sample dyed with two kinds of fluorescence indicators.

The sample S is dyed with the fluorescence indicator (FITC). The fluorescence indicator has, for example, absorption wavelength spectral characteristics shown in FIG. 2. There are two manners of acquiring the absorption wavelength spectral characteristics of the sample S: (a) acquisition of the absorption wavelength spectral characteristics within a certain region M on the sample S as shown in FIG. 3; and (b) acquisition of the absorption wavelength spectral characteristics at each pixel (each of positions C, D, E) on the fluorescent image data of the sample S as shown in FIG. 4.

(a) Acquisition of the absorption wavelength spectral characteristics within a certain region M will be first described.

A wavelength range (for example, 400 nm to 550 nm) to acquire the absorption wavelength spectral characteristics, the wavelength resolution (for example, 1 nm) and coordinates of the scanning region (for example, region M in FIG. 3) of the laser beam which is scanned on the surface of the sample S, are input by using the operation input unit 57.

The control box 55 stores the wavelength range (for example, 400 nm to 550 nm), the wavelength resolution (for example, 1 nm) and the coordinates of the scanning region (for example, region M) of the laser beam, which are input by the operation input unit 57, in the internal memory 58.

The laser oscillator 41 oscillates the pulse laser beam Lp. The oscillated pulse laser beam Lp is converted into the wideband spread spectrum light beam Lp' by the optical device 42. The spread spectrum light beam Lp' is reflected at the mirror 43 and made incident on the AOTF 44.

The wavelength variation control unit 60 transmits the wavelength control signal to successively vary the wavelength in a range of, for example, 400 nm to 550 nm, to the AOTF controller 45. The AOTF controller 45 inputs the wavelength control signal transmitted from the wavelength variation control unit 60 and supplies the RF signal corresponding to the selected wavelength to the AOTF 44. The AOTF 44 receives the RF signal from the AOTF controller 45, selects the successively varied wavelength in a range of, for example, 400 nm to 550 nm, from the spread spectrum light beam Lp', and outputs the spectrum Ls of the selected wavelength.

The spectrum Ls is made incident on the XY scanner 46. The XY scanner 46 scans the spectrum Ls in accordance with the coordinates of the scanning region over the surface of the sample S. The XY scanner 46 performs, for example, raster scanning of the spectrum Ls. The spectrum Ls is passed through the pupil projection lens 47, the mirror 48, the image-forming lens 49 and the objective 50, and scanned on the designated scanning region over the surface of the sample S.

When the spectrum Ls is applied to the fluorescence indicator of the sample S by the raster scanning of the spectrum Ls on the surface of the sample S, the fluorescence indicator is excited. The fluorescence is radiated from the excited fluorescence indicator.

The fluorescence from the sample S is passed through the objective 50, the image-forming lens 49, the mirror 48, the pupil projection lens 47 and the XY scanner 46, and made incident on the AOTF 44. The fluorescence is further passed through the AOTF 44, the confocal lens 51, the confocal aperture 52 and the laser cut filter 53, and made incident on the photoelectric conversion device 54. The photoelectric conversion device 54 outputs the light quantity detection signal in accordance with the quantity of the received fluorescence.

The data acquisition unit 61 of the control box 55 inputs the light quantity detection signal which is sequentially output from the photoelectric conversion device 54 while synchronizing with the wavelength selection of the AOTF 44, sequentially acquires the fluorescence quantity data from the light quantity detection signal and stores the data in the internal memory 58. The fluorescence quantity data stored in the internal memory 58 corresponds to the scanning position over the sample S subjected to raster scanning. Thus, the fluorescence quantity data in the wavelength range (for example, 400 nm to 550 nm) in which the absorption wavelength spectral characteristics are obtained is acquired.

When the data acquisition unit 61 has terminated acquisition of the fluorescence quantity data in the certain region on the sample S, the data acquisition unit 61 acquires the absorption wavelength spectral characteristics by performing an operation of the fluorescence quantity data and stores the acquired absorption wavelength spectral characteristics in the internal memory 58.

The control box 55 converts the fluorescence quantity data into the fluorescent image data and displays the fluorescent image data on the display unit 56 such as a CRT display.

The control box 55 reads the absorption wavelength spectral characteristics of the sample S stored in the internal memory 58, converts the absorption wavelength spectral characteristics into the image data and displays the image data on the display unit 56 such as a CRT display.

(b) Acquisition of the absorption wavelength spectral characteristics at each pixel will be described.

A wavelength range (for example, 400 nm to 550 nm) to acquire the absorption wavelength spectral characteristics, a wavelength resolution (for example, 1 nm) and coordinates of the scanning region (for example, coordinates of pixel positions C, D and E in FIG. 4) corresponding to one pixel of the laser beam scanned on the surface of the sample S, are input by using the operation input unit 57.

The control box 55 stores the wavelength range (for example, 400 nm to 550 nm), the wavelength resolution (for example, 1 nm) and the coordinates of the scanning region (for example, coordinates of pixel positions C, D and E) of the laser beam corresponding to one pixel, which are input by the operation input unit 57, in the internal memory 58.

The pulse laser beam Lp oscillated from the laser oscillator 41 is converted into the wideband spread spectrum light beam Lp' by the optical device 42. The spread spectrum light beam Lp' is reflected at the mirror 43 and made incident on the AOTF 44.

The wavelength variation control unit 60 transmits the wavelength control signal to successively vary the wavelength in a range of, for example, 400 nm to 550 nm, to the AOTF controller 45. The AOTF 44 selects the successively varied wavelength in a range of, for example, 400 nm to 550 nm, from the spread spectrum light beam Lp' and outputs the spectrum Ls of the selected wavelength, in a manner similar to the above-described manner.

The spectrum Ls is subjected to raster scanning on the basis of, for example, the coordinates of the scanning region of the 1-pixel position C over the surface of the sample S, by the XY scanner 46. The spectrum Ls is passed through the pupil projection lens 47, the mirror 48, the image-forming lens 49 and the objective 50, and scanned on the designated scanning region over the surface of the sample S.

When the spectrum Ls is subjected to raster scanning in the scanning region of the 1-pixel position C on the surface of the sample S, the fluorescence indicator is excited. The fluorescence is radiated from the excited fluorescence indicator.

The fluorescence from the sample S is passed through the objective 50, the image-forming lens 49, the mirror 48, the pupil projection lens 47, the XY scanner 46, the AOTF 44, the confocal lens 51, the confocal aperture 52 and the laser cut filter 53, and made incident on the photoelectric conversion device 54. The photoelectric conversion device 54 outputs the light quantity detection signal in accordance with the quantity of the received fluorescence.

The data acquisition unit 61 inputs the light quantity detection signal sequentially output from the photoelectric conversion device 54 by synchronizing with the wavelength selection of the AOTF 44, sequentially acquires the fluorescence quantity data from the light quantity detection signal and stores the data in the internal memory 58. The fluorescence quantity data stored in the internal memory 58 corresponds to the scanning position of the 1-pixel position C over the sample S.

Next, when pixel position D is determined, the XY scanner 46 performs raster scanning of the spectrum Ls on the basis of the coordinates of the pixel position D. Thus, the fluorescence quantity data is stored in the internal memory 58.

Furthermore, the fluorescence quantity data at each pixel position E is stored in the internal memory 58.

When the data acquisition unit 61 has terminated acquisition of the fluorescence quantity data at each of the pixel positions C, D and E, the data acquisition unit 61 acquires the absorption wavelength spectral characteristics at each of the pixel positions C, D and E by performing an operation of the fluorescence quantity data and stores the acquired absorption wavelength spectral characteristics in the internal memory 58.

The control box 55 converts the fluorescence quantity data at each of the pixel positions C, D and E into the fluorescent image data and displays the fluorescent image data on the display unit 56 such as a CRT display.

The control box 55 reads the absorption wavelength spectral characteristics at each of the pixel positions C, D and E stored in the internal memory 58, converts the absorption wavelength spectral characteristics into the image data and displays the image data on the display unit 56 such as a CRT display.

Next, discrimination of the kind of fluorescence indicator dyeing the sample S will be described.

The sample S is dyed with two kinds of fluorescence indicators Y and Z as shown in FIG. 4. In the fluorescent image data shown in the figure, the pixel position C is dyed with fluorescence indicator Y. The pixel position D is dyed with fluorescence indicator Z. The pixel positions C and D are sites which are apparently dyed with fluorescence indicators Y and Z, respectively.

The pixel position E is a site to discriminate which kind of fluorescence indicator dyes the sample S.

The absorption wavelength spectral characteristic $A_C(\lambda)$ of the pixel position C and the absorption wavelength spectral characteristic $A_D(\lambda)$ of the pixel position D are used as reference data to discriminate the kind of fluorescence indicator dyeing the site of the pixel position E.

The absorption wavelength spectral characteristics $A_C(\lambda)$ and $A_D(\lambda)$ of the respective pixel positions C and D may be acquired by actual measurement in the above-described method (a) or (b). In addition, released data of each of known fluorescence indicators Y and Z may be used as the absorption wavelength spectral characteristics $A_C(\lambda)$ and $A_D(\lambda)$.

When the absorption wavelength spectral characteristics $A_C(\lambda)$ and $A_D(\lambda)$ are actually measured, for example, an observer observes the image of the fluorescent image data displayed on the display unit 56 such as a CRT display. The observer determines the site which individually emits the fluorescence by each of fluorescence indicators Y and Z, in the image of the fluorescent image data. After that, the observer inputs the coordinates of the sites by the operation input unit 57.

The control box 55 reads the fluorescence quantity data of the coordinates input by the operation input unit 57, performs an operation of the fluorescence quantity data and acquires the absorption wavelength spectral characteristics $A_C(\lambda)$ and $A_D(\lambda)$ of the respective pixel positions C and D.

In acquiring the absorption wavelength spectral characteristics $A_C(\lambda)$ and $A_D(\lambda)$, a laser cut filter 53 corresponding to the fluorescence wavelength of fluorescence indicator Z is employed to prevent the excited wavelength of fluorescence indicator Z from being detected by the photoelectric conversion device 54.

Figure 5:
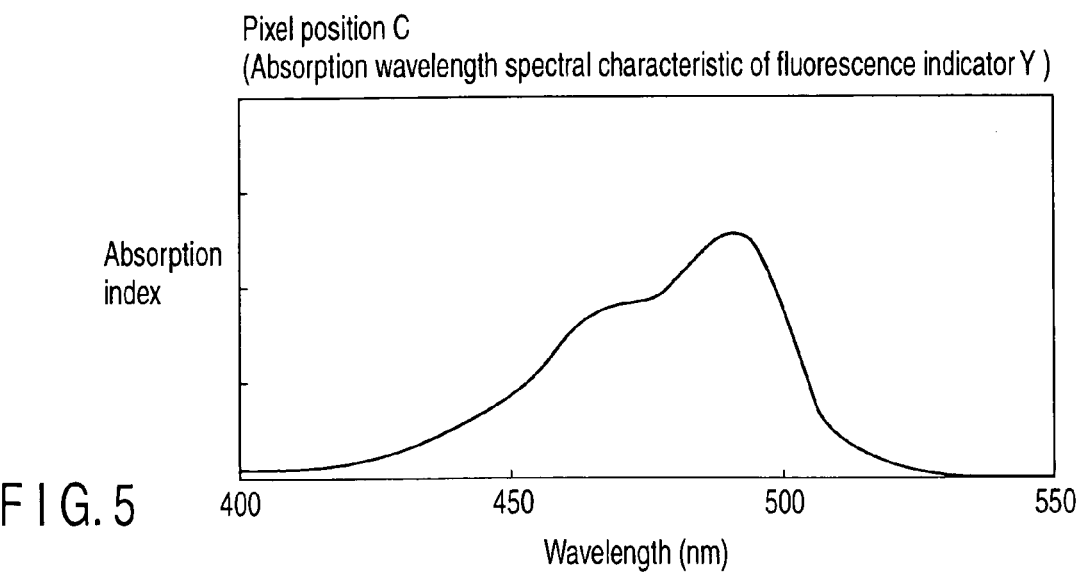
FIG. 5 is a graph showing the absorption wavelength spectral characteristics of fluorescence indicator Y.
Figure 6:
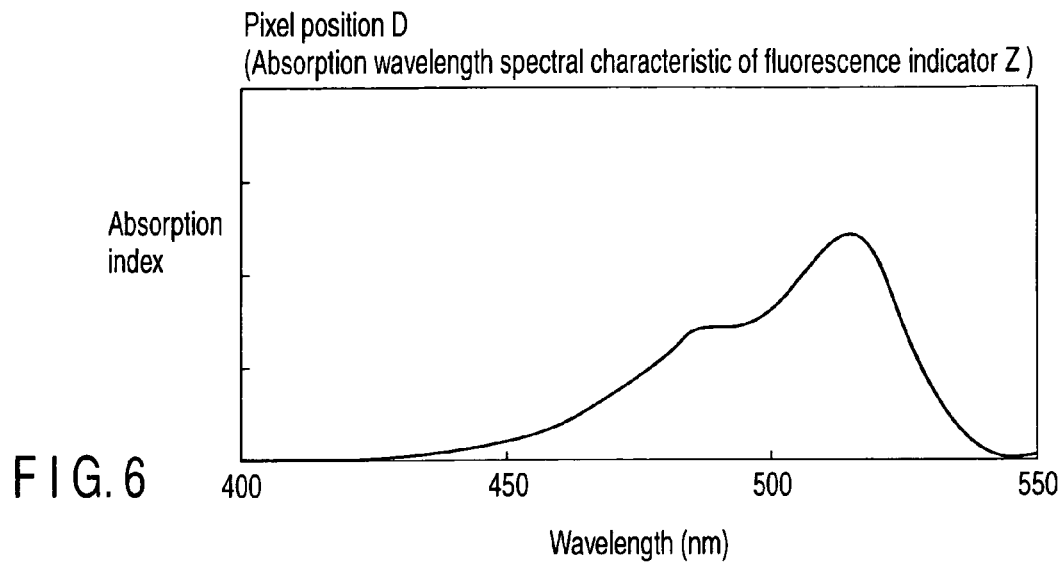
FIG. 6 is a graph showing the absorption wavelength spectral characteristics of fluorescence indicator Z.

FIG. 5 shows the absorption wavelength spectral characteristic $A_C(\lambda)$ of fluorescence indicator Y at the pixel position C. FIG. 6 shows the absorption wavelength spectral characteristic $A_D(\lambda)$ of fluorescence indicator Z at the pixel position D.

To acquire the absorption wavelength spectral characteristic $A_E(\lambda)$ of the pixel position E to be discriminated, the above-described method (a) or (b) is employed.

When the absorption wavelength spectral characteristic $A_E(\lambda)$ of the pixel position E is actually measured, for example, an observer observes the image of the fluorescent image data displayed on the display unit 56 such as a CRT display. The observer determines the site of the pixel position E, in the image of the fluorescent image data. After that, the observer inputs the coordinates of the determined site by the operation input unit 57.

The control box 55 reads the fluorescence quantity data of the coordinates input by the operation input unit 57, performs an operation of the fluorescence quantity data and acquires the absorption wavelength spectral characteristic $A_E(\lambda)$ of the pixel position E.

Figure 7:
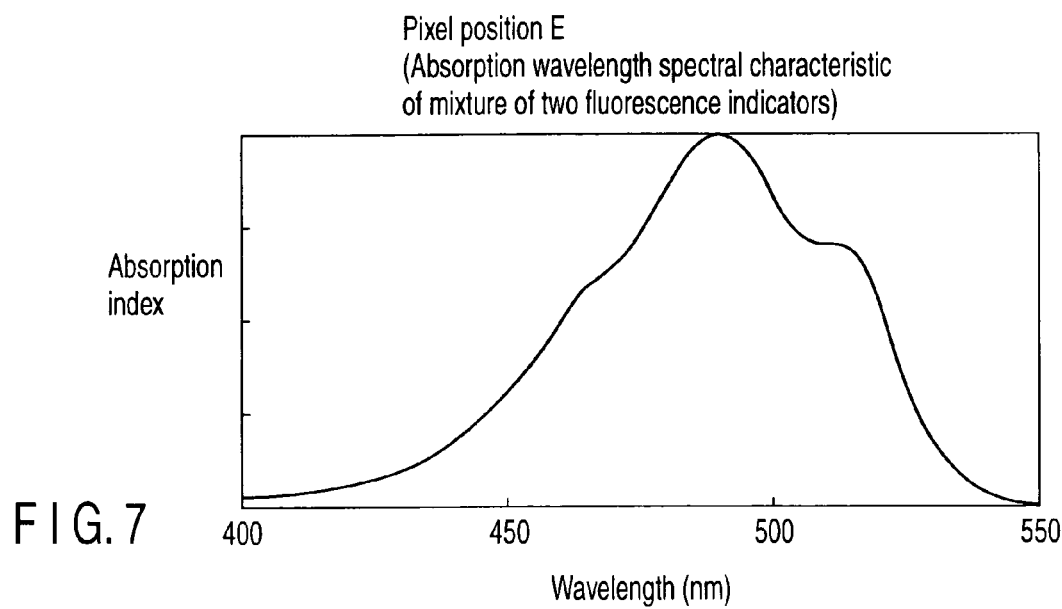
FIG. 7 is a graph showing the absorption wavelength spectral characteristics of mixed fluorescence indicators Y and Z.
Figure 10:
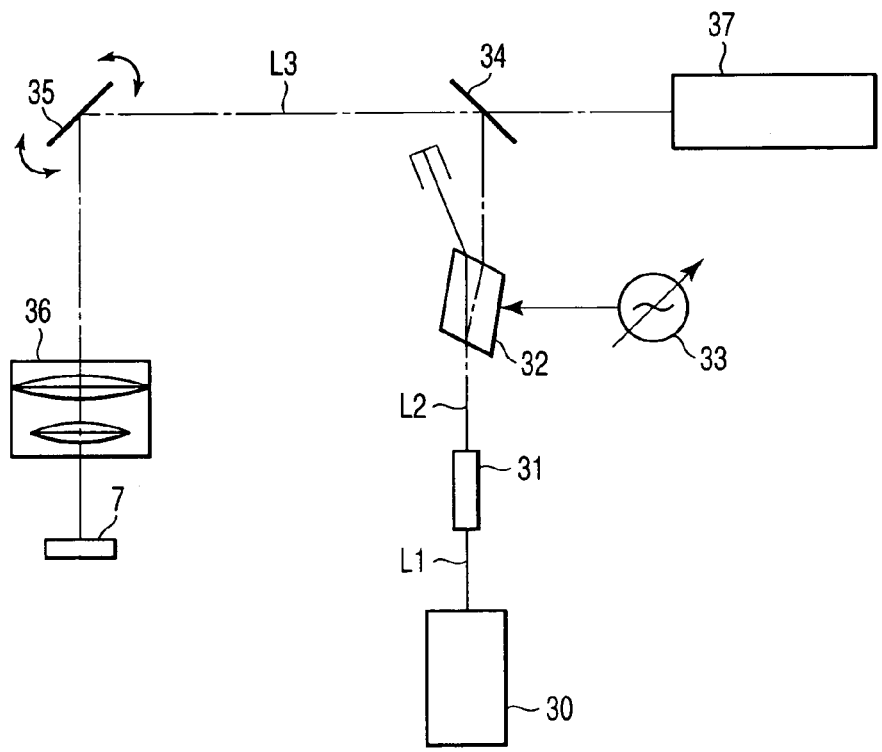
FIG. 10 is a diagram showing a structure of a conventional scanning microscope.
Figure 9:
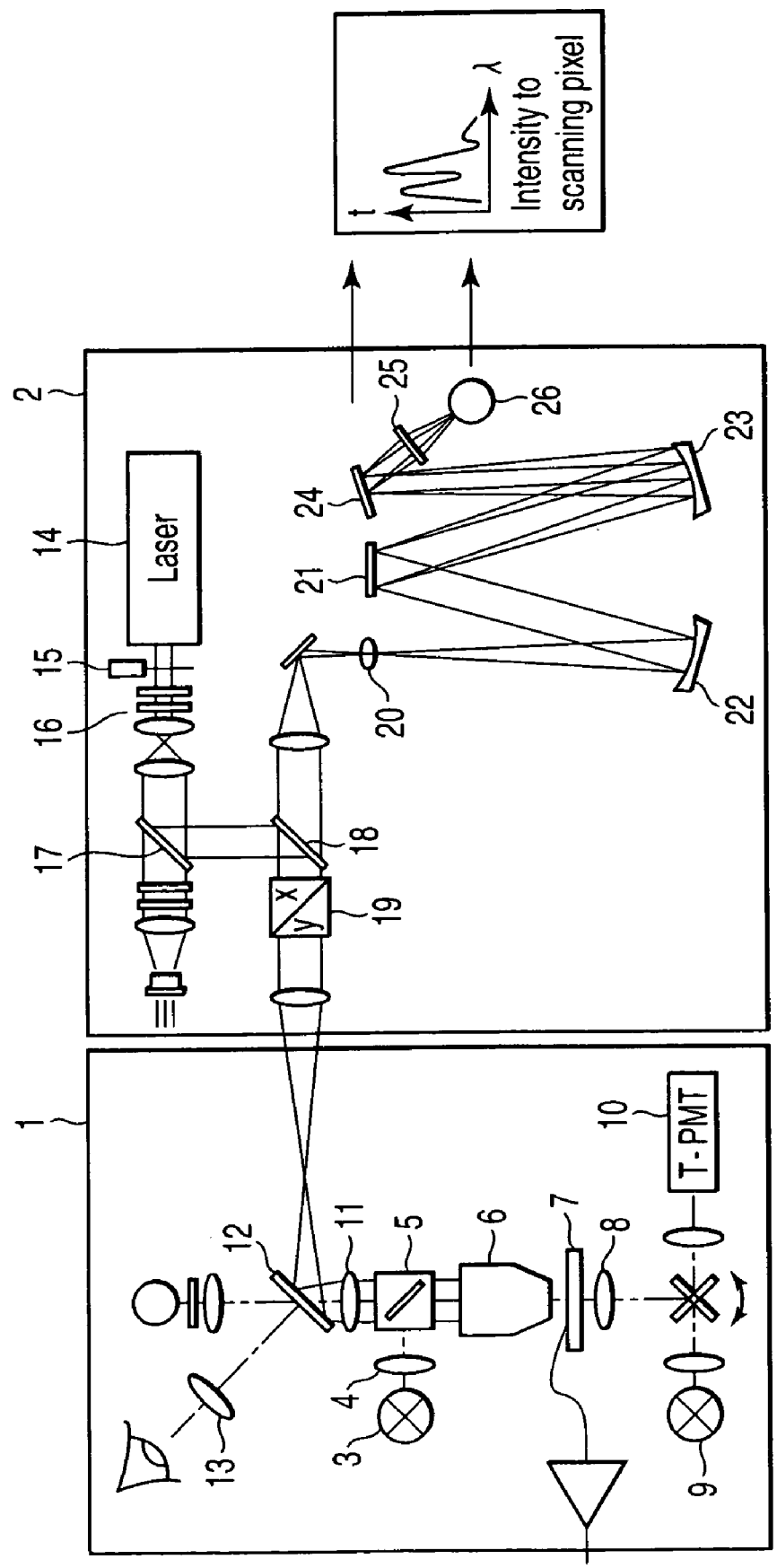
FIG. 9 is a diagram showing a structure of a conventional laser scanning microscope.

FIG. 7 shows the absorption wavelength spectral characteristic $A_E(\lambda)$ of the pixel position E.

Next, the discriminating unit 62 of the control box 55 divides the absorption wavelength spectral characteristic $A_E(\lambda)$ of the pixel position E by the absorption wavelength spectral characteristics $A_C(\lambda)$ and $A_D(\lambda)$ of the respective pixel positions C and D which are handled as the reference data. The division is represented by the following mathematical expressions (1) to (3):

$$k_C(\lambda) = A_E(\lambda)/A_C(\lambda) \quad (1)$$

$$k_D(\lambda) = A_E(\lambda)/A_D(\lambda) \quad (2)$$

$$k_{C+D}(\lambda) = A_E(\lambda)/\{A_C(\lambda) + A_D(\lambda)\} \quad (3)$$

Each of the absorption wavelength spectral characteristics $A_C(\lambda)$, $A_D(\lambda)$ and $A_E(\lambda)$ is a function of the excited wavelength $\lambda$. A result from each of the divisions represented by the expressions (1) to (3) is a function of the excited wavelength $\lambda$.

If either the expression (1) or (2) represents a constant value irrespective of the excited wavelength $\lambda$ as a result of the division in the expressions, the discriminating unit 62 discriminates that the absorption wavelength spectral characteristic $A_E(\lambda)$ of the pixel position E is the same as the absorption wavelength spectral characteristic of fluorescence indicator Y or Z in the expression (1) or (2) indicating the constant value.

As a result, the discriminating unit 62 discriminates that the pixel position E is dyed with fluorescence indicator Y alone if the expression (1) indicates the constant value or that the pixel position E is dyed with fluorescence indicator Z alone if the expression (2) indicates the constant value.

If the expression (3) indicates the constant value irrespective of the excited wavelength $\lambda$, the discriminating unit 62 discriminates that the pixel position E is dyed fluorescence indicators Y and Z.

When any of the expressions indicates the constant value, a value of division $k_C(\lambda)$, $k_D(\lambda)$, or $k_{C+D}(\lambda)$ represents a ratio of brightness at the measurement position to the data as the reference data. The control box 55 multiplies the value $k_C(\lambda)$, $k_D(\lambda)$, or $k_{C+D}(\lambda)$ representing the constant value by the absorption wavelength spectral characteristic $A_C(\lambda)$ of the pixel position C as shown by the following mathematical expression (4) in order to obtain the absorption wavelength spectral characteristic of fluorescence indicator Y at the pixel position E.

Absorption wavelength spectral characteristic of fluorescence indicator Y at the pixel position E $$= A_C(\lambda) \cdot k_x(\lambda) \quad (4)$$

The control box 55 multiplies the value $k_C(\lambda)$, $k_D(\lambda)$, or $k_{C+D}(\lambda)$ by the absorption wavelength spectral characteristic $A_D(\lambda)$ of the pixel position C as shown by the following mathematical expression (5) in order to obtain the absorption wavelength spectral characteristic of fluorescence indicator Z at the pixel position D.

Absorption wavelength spectral characteristic of fluorescence indicator Z at the pixel position E $$= A_D(\lambda) \cdot k_x(\lambda) \quad (5)$$

$k_x$ corresponds to $k_C(\lambda)$, $k_D(\lambda)$, or $k_{C+D}(\lambda)$.

In the first embodiment as described above, the spectrum Ls is scanned over the sample S while the wavelength of the spectrum Ls is varied. The quantity of the fluorescence from the sample S is detected to acquire the absorption wavelength spectral characteristics $A_C(\lambda)$ and $A_D(\lambda)$ of respective fluorescence indicators Y and Z whose kinds are known and which dye the sample S. The absorption wavelength spectral characteristic $A_E(\lambda)$ of the discriminated site is compared with each of the absorption wavelength spectral characteristics $A_C(\lambda)$ and $A_D(\lambda)$ of the respective fluorescence indicators whose kinds are known.

The kind of fluorescence indicator dyeing the pixel position E can be discriminated from the comparison result. For example, if the value obtained by dividing the absorption wavelength spectral characteristic $A_E(\lambda)$ of the pixel position E to be discriminated by the absorption wavelength spectral characteristic $A_C(\lambda)$ of the pixel position C dyed with fluorescence indicator Y is the constant value, it can be discriminated that the pixel position E is dyed with fluorescence indicator Y.

If the value obtained by dividing the absorption wavelength spectral characteristic $A_E(\lambda)$ of the pixel position E by the absorption wavelength spectral characteristic $A_D(\lambda)$ of the pixel position D dyed with fluorescence indicator Z is the constant value, it can be discriminated that the pixel position E is dyed with fluorescence indicator Z.

If the value obtained by dividing the absorption wavelength spectral characteristic $A_E(\lambda)$ of the pixel position E by the sum of the absorption wavelength spectral characteristics $A_C(\lambda)$ and $A_D(\lambda)$ of the pixel positions C and D dyed respectively with two kinds of fluorescence indicators Y and Z is the constant value, it can be discriminated that the pixel position E is dyed with two kinds of fluorescence indicators Y and Z.

If the pixel position E is dyed with plural kinds, for example, three kinds of fluorescence indicators Y, Z and Q, the value obtained by dividing the absorption wavelength spectral characteristic $A_E(\lambda)$ of the pixel position E by the sum of the absorption wavelength spectral characteristics $A_C(\lambda)$, $A_D(\lambda)$ and $A_Q(\lambda)$ of three kinds of fluorescence indicators Y, Z and Q is the constant value. Thus, even if the pixel position E is dyed with plural kinds of fluorescence indicators, each of the fluorescence indicators can be discriminated.

The wavelength of the wideband spread spectrum light beam Lp' which is output from the laser light source unit 40 is selected by the AOTF 44. The selected wavelength of the spectrum Ls is successively varied and the spectrum Ls is scanned over the sample S dyed with fluorescence indicators Y and Z. The fluorescence quantity data is detected by the photoelectric conversion device 54 while synchronizing the fluorescence from the sample S with the selected wavelength of the AOTF 44. Thus, the absorption wavelength spectral characteristics of respective fluorescence indicators Y and Z dyeing the sample S can be acquired with a high resolution by performing an operation of the fluorescence quantity data.

The kind of fluorescence indicator dyeing the pixel position E may be discriminated in the following manner.

The absorption wavelength spectral characteristic is obtained by the following expression (6)

$$k(\lambda) = A_E(\lambda)/[R \cdot A_C(\lambda) + (1-R) \cdot A_D(\lambda)] \quad (6)$$

where coefficient R is $0 \leq R \leq 1$.

The discriminating unit 62 obtains the coefficient R that makes $k(\lambda)$ of the expression (6) substantially constant.

The coefficient R is expressed here as $R_0$ where $k(\lambda)$ is substantially constant. If $R_0$ is equal to 0, the expression (6) is equivalent to the expression (2). Thus, the discriminating unit 62 discriminates that the pixel position E is dyed with fluorescence indicator Z alone similarly to the pixel position D.

If $R_O$ is equal to 1, the discriminating unit 62 discriminates that the pixel position E is dyed with fluorescence indicator Y alone similarly to the pixel position C.

If $R_O$ is greater than 0 and smaller than 1, the discriminating unit 62 discriminates that the pixel position E is dyed with two kinds of fluorescence indicators Y and Z.

$R_O$ represents the rate of emitting the fluorescence emitted from two kinds of fluorescence indicators Y and Z. As the value of $R_O$ is smaller, the quantity of the fluorescence emitted from fluorescence indicator Y becomes greater. As the value of $R_O$ is greater, the quantity of the fluorescence emitted from fluorescence indicator Z becomes greater.

$k(\lambda)$ represents the ratio of the brightness of the measured site to the reference data when $k(\lambda)$ is a constant value.

$k(\lambda)$ and R are employed to perform operations of the following expressions (7) and (8). The absorption wavelength spectral characteristics of each of fluorescence indicators Y and Z at the pixel positions E are thereby obtained.

Absorption wavelength spectral characteristic of fluorescence indicator Y at the pixel positions E $$= A_C(\lambda) \cdot R \cdot k(\lambda) \quad (7)$$

Absorption wavelength spectral characteristic of fluorescence indicator Z at the pixel positions E $$= A_D(\lambda) \cdot (1 - R) \cdot k(\lambda) \quad (8)$$

Next, a second embodiment of the present invention will be explained below with reference to the accompanying drawings. Elements like or similar to those disclosed in FIG. 1 are denoted by similar reference numbers and are not described in detail here.

FIG. 8 shows a structure of a laser scanning microscope. The beam splitter 70 is provided in the optical path of the spectrum Ls which selectively output from the AOTF 44. For example, the beam splitter 70 transmits the spectrum Ls at the transmittance of 98% and reflects it at the reflectivity of 2%.

The light detector 71 is provided in the reflected optical path of the beam splitter 70. The light detector 71 receives the spectrum Ls reflected by the beam splitter 70 and outputs the received light quantity signal corresponding to the quantity of the received light.

The light quantity controller 72 inputs the received light quantity signal that is output from the light detector 71 and monitors the quantity of the spectrum Ls. When the light quantity controller 72 discriminates that the quantity of the spectrum Ls has been varied, the light quantity controller 72 transmits the light quantity control signal to the AOTF controller 45 to control the quantity of the spectrum Ls to be constant.

The AOTF controller 45 inputs the light quantity control signal transmitted from the light quantity controller 72 and controls the quantity of each wavelength of the spectrum Ls selected by the AOTF 44, i.e. the quantity of the excited light to be constant.

In the second embodiment as described above, a portion of the spectrum Ls that is output from the AOTF 44 is received by the light detector 71 and the quantity of the received light is monitored. If it is determined by the monitoring that the quantity of the spectrum Ls has been varied, feedback control is performed to control the quantity of the spectrum Ls to be constant.

As a constant quantity of spectrum Ls can be made to dye the sample S, the absorption wavelength spectral characteristics of each of the fluorescence indicators (Y, Z) dyeing the sample S can be acquired at high accuracy. As a result, reliability of discrimination of the fluorescence indicators dyeing the sample S can be improved. Moreover, even if the sample S is dyed with plural kinds of fluorescence indicators, for example, fluorescence indicators Y and Z, each of the absorption wavelength spectral characteristics of the fluorescence indicators Y and Z at the pixel position E can be acquired at high accuracy. As a result, plural kinds of fluorescence indicators, for example, fluorescence indicators Y and Z dyeing the pixel position E can be discriminated.

What is claimed is:

1. A laser scanning microscope comprising:
    a laser output unit which is capable of outputting a laser beam and arbitrarily selecting a wavelength of the laser beam;
    a scanning unit which scans the laser beam output from the laser output unit over a sample having a site dyed with at least one kind of fluorescence indicator;
    a light detector which detects quantity of fluorescence emitted from the sample over which the laser beam is scanned;
    a data acquiring unit which acquires data of the fluorescence quantity detected by the light detector while varying the wavelength of the laser beam output from the laser output unit to obtain absorption wavelength spectral characteristic data of the sample from the fluorescence quantity data; and
    a discriminating unit which discriminates the kind of fluorescence indicator dyeing the site in accordance with scanning position information obtained by scanning the laser beam over the sample by the scanning unit and the absorption wavelength spectral characteristic data.

2. The laser scanning microscope according to claim 1, wherein the site comprises a plurality of first sites each dyed with the known fluorescence indicator alone of one kind and a second site dyed with the fluorescence indicator of at least one kind to be discriminated;
    the data acquiring unit acquires the absorption wavelength spectral characteristic data of each of the first sites and the absorption wavelength spectral characteristic data of the second site; and
    the discriminating unit compares the acquired absorption wavelength spectral characteristic data of each of the first sites and the acquired absorption wavelength spectral characteristic data of the second site, and discriminates the kind of fluorescence indicator to be discriminated in accordance with a result of the comparison.

3. The laser scanning microscope according to claim 2, wherein the discriminating unit divides the absorption wavelength spectral characteristic data of the second site by the absorption wavelength spectral characteristic data of each of the first sites and, if a value of each of the divisions represents a constant value irrespective of variation in the wavelength of the laser beam, the discriminating unit discriminates that the second site is dyed with the known fluorescence indicator corresponding to the absorption wavelength spectral characteristic data of the first site used in the division representing the constant value.

4. The laser scanning microscope according to claim 2, wherein the discriminating unit obtains a value of division by dividing the absorption wavelength spectral characteristic data of the second site by the absorption wavelength spectral characteristic data of each of the first sites, and a value of division by dividing the absorption wavelength spectral characteristic data of the second site by sum of the absorption wavelength spectral characteristic data of the first sites; and the discriminating unit discriminates that the second site is dyed with the known fluorescence indicator of at least one kind corresponding to the absorption wavelength spectral characteristic data of the first sites or the sum of the absorption wavelength spectral characteristic data used in the division whose value represents the constant value.

5. The laser scanning microscope according to claim 4, wherein if the absorption wavelength spectral characteristic data of the first site used in the division corresponds to the sum of the absorption wavelength spectral characteristic data, the discriminating unit discriminates that the second site is dyed with the known fluorescence indicators of plural kinds.

6. The laser scanning microscope according to claim 2, wherein the discriminating unit performs an operation of a relational expression with the absorption wavelength spectral characteristic data of the first sites, the absorption wavelength spectral characteristic data of the second site, and a coefficient for discrimination of the fluorescence indicators of plural kinds, and discriminates the kind of fluorescence indicator dyeing the second site from a result of the operation of the relational expression according to the coefficient.

7. The laser scanning microscope according to claim 1, further comprising:
a beam splitter which takes a portion of the laser beam whose wavelength is selected by the laser output unit;
a light detector which detects the laser beam taken by the beam splitter; and
a light quantity control unit which controls quantity of the laser beam whose wavelength is selected by the laser output unit in accordance with quantity of the portion of the laser beam taken by the beam splitter.

8. The laser scanning microscope according to claim 1, wherein the laser output unit comprises:
a laser oscillator which oscillates the laser beam;
an optical device which converts the laser beam oscillated by the laser oscillator into a spread spectrum light beam; and
a wavelength selecting unit which successively varies a wavelength of the spread spectrum light beam output from the optical device to an arbitrary wavelength.

9. The laser scanning microscope according to claim 8, wherein the optical device comprises a photonic bandgap material.

10. The laser scanning microscope according to claim 8, wherein the wavelength selecting unit comprises:
an acousto-optic element; and
a wavelength control unit which supplies a radio frequency signal to the acousto-optic element successively varies a wavelength of the spread spectrum light beam output from the acousto-optic element.

11. The laser scanning microscope according to claim 1, wherein the scanning unit scans the laser beam within a certain region on the sample.

12. The laser scanning microscope according to claim 1, wherein the scanning unit scans the laser beam within a certain region on the sample corresponding to a 1-pixel region of the fluorescence quantity data.

13. The laser scanning microscope according to claim 1, wherein the light detector detects the quantity of the fluorescence emitted from the sample, synchronously with the selection of the wavelength of the laser beam performed by the laser output unit.

14. The laser scanning microscope according to claim 1, wherein the absorption wavelength spectral characteristic data is input by each of the fluorescence indicators of plural kinds, in the data acquiring unit.

15. The laser scanning microscope according to claim 1, wherein the absorption wavelength spectral characteristic data is stored by each of the fluorescence indicators of plural kinds, in the data acquiring unit.

16. A laser scanning microscope comprising:
a laser output unit which is capable of outputting a laser beam and arbitrarily selecting a wavelength of the laser beam;
a scanning unit which scans the laser beam output from the laser output unit over a sample having a site dyed with at least one kind of fluorescence indicator;
a light detector which detects quantity of fluorescence emitted from the sample over which the laser beam is scanned; and
a data acquiring unit which acquires data of the fluorescence quantity detected by the light detector while varying the wavelength of the laser beam output from the laser output unit to obtain absorption wavelength spectral characteristic data of the sample from the fluorescence quantity data.

17. A method of discriminating a fluorescence indicator, comprising:
scanning a laser beam over a sample dyed with a fluorescence indicator while varying a wavelength of the laser beam;
measuring quantity of fluorescence emitted from at least a site of the sample to be measured;
acquiring an absorption wavelength spectral characteristic of the measured site from the quantity of the fluorescence;
acquiring absorption wavelength spectral characteristic data of a plurality of known fluorescence indicators whose kinds are known and which dye the sample; and
comparing the absorption wavelength spectral characteristic data of the measured site with the absorption wavelength spectral characteristic data of the fluorescence indicators whose kinds are known, and discriminating the kind of fluorescence indicator dyeing the measured site from a result of the comparison.

18. The method according to claim 17, wherein the absorption wavelength spectral characteristic data of the fluorescence indicators of plural kinds is acquired by each of the sites that is dyed with the fluorescence indicator alone of one kind.

19. The method according to claim 17, wherein as the absorption wavelength spectral characteristic data of the fluorescence indicators of plural kinds, the absorption wavelength spectral characteristic data preliminarily input by each of the fluorescence indicators by the laser scanning microscope is employed.

20. The method according to claim 17, wherein as the absorption wavelength spectral characteristic data of the fluorescence indicators of plural kinds, the absorption wavelength spectral characteristic data prestored by each of the fluorescence indicators is employed.

* * * * *